US008283015B2

(12) United States Patent
Chauhan et al.

(10) Patent No.: US 8,283,015 B2
(45) Date of Patent: Oct. 9, 2012

(54) AUTHENTICATABLE ARTICLES AND METHODS THEREFOR

(75) Inventors: Yogendrasinh Bharatsinh Chauhan, Gujarat (IN); Adil Minoo Dhalla, Maharashtra (IN); Sriramakrishna Maruvada, Evansville, IN (US); Shantaram Narayan Naik, Karnataka (IN); Vandita Pai-Paranjape, Evansville, IN (US); Kiran Puthamane, Maharashtra (IN); Philippe Schottland, West Chester, OH (US)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 13/088,855

(22) Filed: Apr. 18, 2011

(65) Prior Publication Data
US 2011/0196075 A1    Aug. 11, 2011

Related U.S. Application Data

(63) Continuation of application No. 11/536,821, filed on Sep. 29, 2006, now abandoned.

(51) Int. Cl.
*B32B 3/02* (2006.01)
*G11B 7/252* (2006.01)

(52) U.S. Cl. ............... 428/64.4; 428/64.7; 428/64.8; 428/412; 428/913; 428/916

(58) Field of Classification Search ............... 428/64.4, 428/64.8, 64.7, 412, 913, 916
See application file for complete search history.

(56) References Cited

U.S. PATENT DOCUMENTS

| | | | |
|---|---|---|---|
| 3,066,105 A | 11/1962 | McCafferty | |
| 3,162,642 A | 12/1964 | McCafferty | |
| 3,164,503 A | 1/1965 | Gehrig | |
| 3,164,603 A | 1/1965 | McCafferty | |
| 3,723,449 A | 3/1973 | Wirth | |
| 4,707,297 A | 11/1987 | Paske, Jr. et al. | |
| 5,005,873 A | 4/1991 | West | |
| 5,277,839 A | 1/1994 | Schultz | |
| 5,326,692 A | 7/1994 | Brinkley et al. | |
| 5,482,986 A | 1/1996 | Ogiso et al. | |
| 6,099,930 A | 8/2000 | Cyr et al. | |
| 6,177,572 B1 | 1/2001 | Wang | |
| 6,514,617 B1 * | 2/2003 | Hubbard et al. | 428/412 |
| 6,589,626 B2 | 7/2003 | Selinfreund et al. | |
| 6,771,578 B2 | 8/2004 | Cradic et al. | |
| 6,960,607 B2 | 11/2005 | Malamas et al. | |
| 7,094,364 B2 | 8/2006 | Potyrailo et al. | |
| 2003/0005304 A1 | 1/2003 | Lawandy et al. | |
| 2005/0110978 A1 | 5/2005 | Potyrailo et al. | |
| 2005/0112768 A1 | 5/2005 | Evans et al. | |
| 2005/0272789 A1 | 12/2005 | Hale et al. | |
| 2007/0037785 A1 | 2/2007 | Ansorge et al. | |

FOREIGN PATENT DOCUMENTS

| | | |
|---|---|---|
| EP | 1402888 A1 | 3/2004 |
| WO | 0014736 A1 | 3/2000 |
| WO | 2004067480 A2 | 8/2004 |
| WO | 2005037779 A2 | 4/2005 |
| WO | 2007042816 A1 | 4/2007 |

OTHER PUBLICATIONS

Anthony, Kevin et al., "Solid-State Fluorescent Photophysics of some 2-Substituted Benzothiazoles", Journal of the Chemical Society, Perkin Transactions II, 1984, pp. 2111-2117 (XP009011528).
Campo, Leandra Franciscato et al., "Spectral Properties of Amorphous Silica (SiO2) and Mesoporous Structured Silicates (MCM-41) and ITQ-6 Functionalized with ESIPT Chromophores", Journal of Photochemistry and Photobiology, A: Chemistry, 178 (2006) pp. 26-32, Elsevier.
Campo, Leandra Franciscato et al., "New Fluorescent Monomers and Polymers Displaying an Intromolecular Proto-transfer Mechanism in the Electronically Excited State (ESIPT). IV. Synthesis of Acryloylamide and Diallylamino Benzazole Dyes and its Copolymerization with MMA", Journal of Applied Polymer Science, vol. 99, (2006), pp. 2109-2116, Wiley Periodicals, Inc. (XP002460356).
Dayam, Raveendra et al., "Diketo Acid Pharmsophore. 2. Discovery of Structurally Diverses Inhibitors of HIV-1 Integrase", Journal of Medicinal Chemistry, vol. 48 (2005), pp. 8009-8015, American Chemical Society (XP002412213).
Kondratov, Roman V., et al., "Small Molecules that Dramatically Alter Multidrug Resistance Phenotype by Modulating the Substrate Specificity of P-glycoprotein" Proceedings of the National Academy of Sciences of USA, National Academy of Science, Washington, D.C., vol. 98, No. 24, Nov. 20, 2001, pp. 14078-14083 (XP002259950).

(Continued)

*Primary Examiner* — Gerard Higgins
(74) *Attorney, Agent, or Firm* — Richard M. Klein; Fay Sharpe LLP

(57) ABSTRACT

An article comprising the compound of Formula (I):

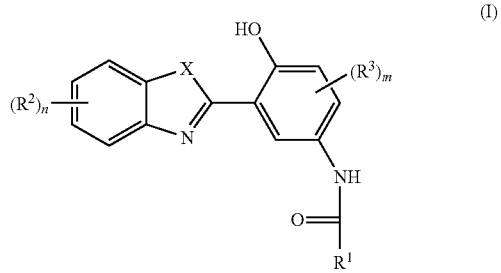

wherein $R^1$ is selected from the group consisting of an aliphatic functionality having 1 to 12 carbons, an aromatic functionality having 3 to 20 carbons, and a cycloaliphatic functionality having 3 to 20 carbons; $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3.

13 Claims, No Drawings

OTHER PUBLICATIONS

Rodembusch, Fabiano Severo et al., The Firtst Silica Aerogels Fluorescent by Excited State Intramolecular Proton Transfer Mechanism (ESIPT), Journal of Materials Chemistry, vol. 15, No. 15, (2005) pp. 1537-1541 (XP002460355).

Database CAPLUS, Chemical Abstract Service, Columbia, Ohio, Barashkov, N. et al., "Design of New Polymers to Improve Radiation Stability of Plastic Scintillators" XP002460357 (1 page).

STN search history of compounds according to Formula (I), created on May 24, 2010.

International Search Report for PCT/US2007/074566 (Reference No. 191313-1) International Filing Date Jul. 27, 2007, Mailing Date Dec. 14, 2007 (7 pages).

Written Opinion of the International Searching Authority for PCT/US2007/074566 (Reference No. 191313-1) International Filing Date Jul. 27, 2007, Mailing Date Dec. 14, 2007 (8 pages).

International Search Report for PCT/US2007/074572 (Reference No. 191313-2) International Filing Date Jul. 27, 2007, Mailing Date 14/12/20078 (6 Pages).

Written Opinion of the International Searching Authority for PCT/US2007/074572 (Reference No. 191313-2) International Filing Date Jul. 27, 2007, Mailing Date Dec. 14, 2007 (7 Pages).

\* cited by examiner

AUTHENTICATABLE ARTICLES AND METHODS THEREFOR

This application is a continuation of U.S. patent application Ser. No. 11/536,821, filed Sep. 29, 2006 now abandoned. The disclosure of that application is hereby fully incorporated by reference herein.

BACKGROUND

The present disclosure generally relates to authenticatable articles. More particularly the disclosure relates to authenticatable articles comprising benzoxazole and benzothiazole compounds. These benzoxazole and/or benzothiazole compounds are useful as authentication compounds in the authenticatable articles.

Polymers, such as polycarbonates are widely used as substrates in a variety of data storage media or optical storage media. These media traditionally contain information such as machine-readable codes, audio, video, text, and/or graphics. One major problem confronting the various makers and users of data storage media is the unauthorized reproduction or copying of information by unauthorized manufacturers, sellers and/or users. Such unauthorized reproduction or duplication of data storage media is often referred to as piracy. Piracy can occur at various instances, such as at the consumer level at the point of end use, or at a commercial level where wholesale duplication of valuable information stored in a data storage medium can take place. Regardless of the manner, piracy of data storage media deprives legitimate content providers, such as software and entertainment content providers, as well as original electronic equipment manufacturers, of significant revenue and profit.

One anti-piracy/authentication method aimed at combating these consumer and commercial level reproduction and copying practices involves the placement of 'tags' or authentication markers in substrates used in the construction of data storage media. For example a near-infrared fluorophore can be incorporated into the compact disc via coating, admixing, blending or copolymerization. Fluorescence is detectable when the fluorophore is exposed to electromagnetic radiation having a wavelength ranging from 670 nanometers (nm) to 1100 nm. Other examples include a polymer comprising a tagging material wherein the tagging material comprises an organic fluorophore dye, an inorganic fluorophore, an organometallic fluorophore, a semi-conducting luminescent nanoparticle, or combination thereof, wherein the tagging material has a temperature stability of at least about 350° C. and is present in a sufficient quantity such that the tagging material is detectable via a spectrofluorometer at an excitation wavelength from about 100 nm to about 1100 nm. Some authentication methods rely on one or more intrinsic physical or chemical characteristics of the substrate materials to distinguish unauthorized duplications of information-carrying substrates. Such anti-piracy characteristics may be based on performance characteristics such as (for example in the case of an optical disc) the weight and/or density of the disc; the spin rate of the disc; the acceleration and deceleration of the disc; the inertia of the disc; the spectral characteristics such as reflectance of the disc; the optical characteristics such as light transmittance of the disc; the water absorption and dimensional stability of the disc; the data transfer rate of the disc; and the degree of wobble of the disc, or combinations of such characteristics.

Some other authentication methods include obtaining the chromatic variation of objects in response to external stimuli, the method comprising the incorporation in the desired objects of various pigments having combined effects comprising a luminescent pigment, a thermochromic pigment permitting the change in the color according to the temperature and/or a hygroscopic pigment that will provoke a variation in the chromatic characteristics according to humidity. Thermochromic polymer-based temperature indicator composition that comprises a polythiophene and a carrier medium are also known to be used as authentication methods. The composition is characterized in that the polythiophene is present in the medium in an amount of about 0.05 percent to about 5.0 percent by weight based on the weight of the composition. The structure of the compound is designed such that when the composition is placed in a heat exchange relationship with an article, the composition will exhibit a color change when a design temperature or a temperature beyond the design temperature is reached in the article.

Numerous anti-piracy/authentication methods have been developed and continue to be developed. Manufacturers and users of data storage media continue to seek authenticatable articles that are currently unknown and/or unavailable to unauthorized manufacturers, sellers and/or users of data storage media or data storage media substrates. Further, there is a need for authenticatable articles that will be difficult for unauthorized vendors and producers to obtain, reproduce, use and/or find.

BRIEF SUMMARY

Disclosed herein is an article comprising the compound of Formula (I):

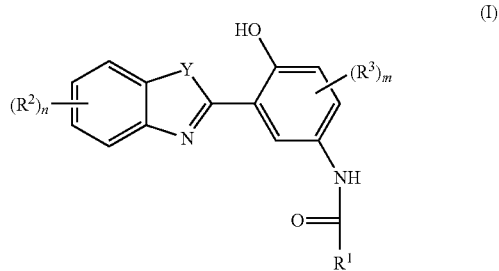

wherein $R^1$ is selected from the group consisting of an aliphatic functionality having 1 to 12 carbons, an aromatic functionality having 3 to 20 carbons, and a cycloaliphatic functionality having 3 to 20 carbons; $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3. In an embodiment, the article may further comprise a second compound of Formula (I). The first and second compound of Formula (I) can be the same or different. In an embodiment, the first and second compound of Formula (I) are different.

In one embodiment, an article comprising a compound selected from the group consisting of Formula (II), Formula (III), Formula (IV), Formula (V), Formula (VI), Formula (VII), Formula (VIII), Formula (IX), and Formula (X):

(II) 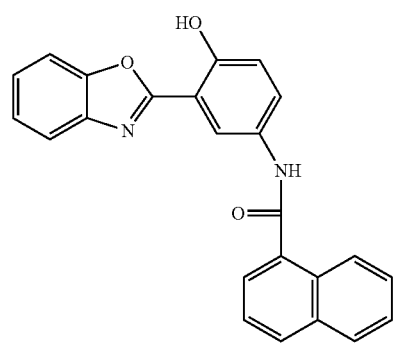
(III) 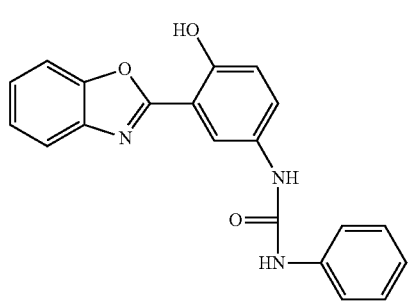
(IV) 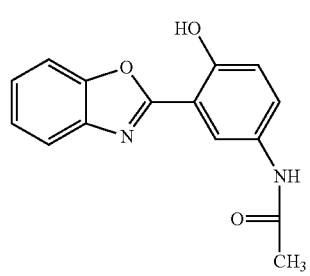
(V) 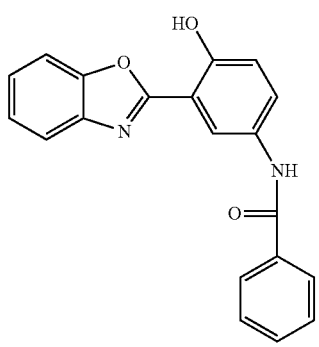
(VI) 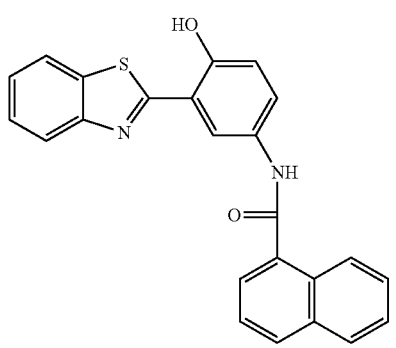
(VII) 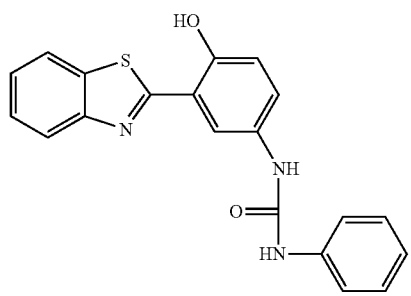
(VIII) 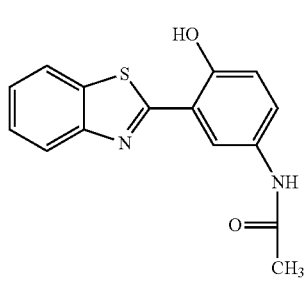
(IX) 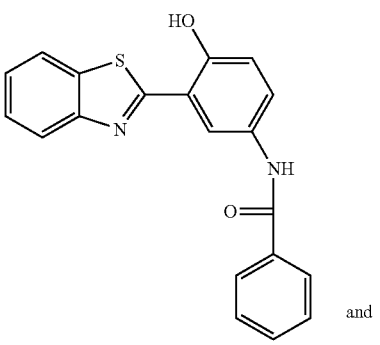
and
(X) 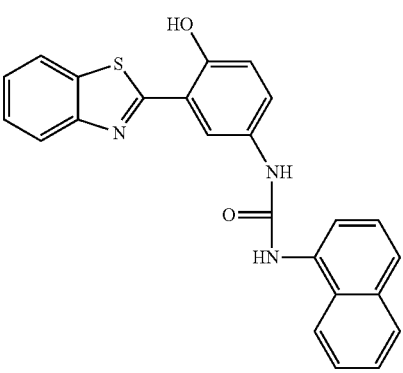
is disclosed.

In another embodiment, an article comprising a benzoxazole compound of Formula (II)

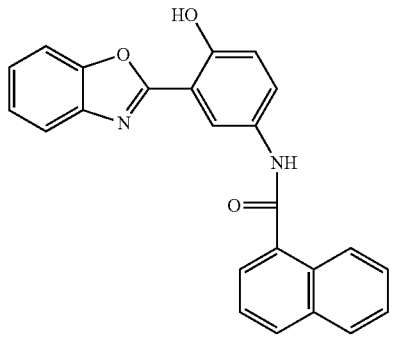

(II)

is disclosed.

In another embodiment, an article comprising a benzoxazole compound of Formula (III):

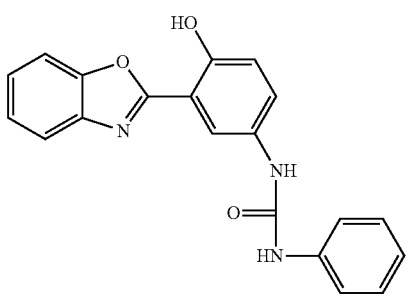

(III)

is disclosed.

In yet another embodiment, an article comprising a benzothiazole compound of Formula (VI):

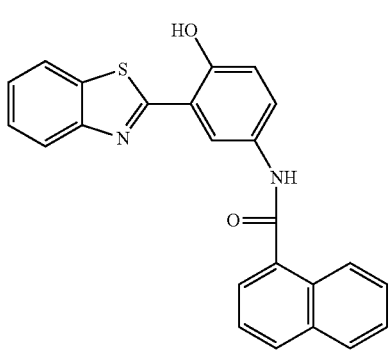

(VI)

is disclosed.

In still yet another embodiment, an article comprising a benzothiazole compound of Formula (VII):

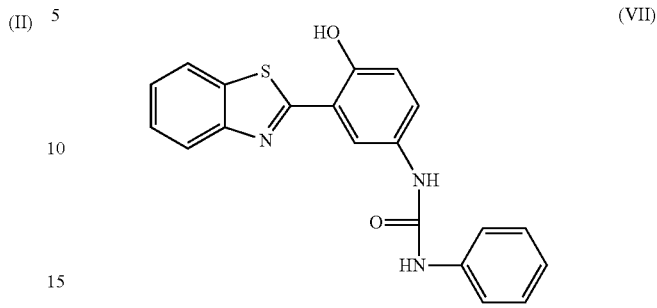

(VII)

is disclosed.

In another embodiment, a method for making an article is provided.

In another embodiment, an authentication method is provided.

The disclosure may be understood more readily by reference to the following detailed description and the examples included therein.

DETAILED DESCRIPTION

Disclosed herein are authenticatable articles containing benzoxazole and benzothiazole compounds. These benzoxazole and/or benzothiazole compounds serve as authentication compounds in the authenticatable articles.

The singular forms "a", "an" and "the" include plural referents unless the context clearly dictates otherwise. All ranges disclosed herein are inclusive of the recited endpoint and independently combinable (for example ranges of "from about 2 grams to about 10 grams" is inclusive of the endpoints and all the intermediate values of the ranges of 2 grams to about 10 grams).

The modifier "about" used in connection with a quantity is inclusive of the stated value and has the meaning dictated by the context (for example, includes the degree of error associated with the measurement of the particular quantity).

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "cycloaliphatic functionality" designates cyclic aliphatic functionalities having a valence of at least one and comprising an array of atoms which is cyclic but which is not aromatic. A cycloaliphatic functionality may comprise one or more noncyclic components. For example, a cyclohexylmethyl group ($C_6H_{11}CH_2$) is a cycloaliphatic functionality, which comprises a cyclohexyl ring (the array of atoms which is cyclic but which is not aromatic) and a methylene group (the noncyclic component). The cycloaliphatic functionality may include heteroatoms such as nitrogen, sulfur, selenium, silicon and oxygen, or may be composed exclusively of carbon and hydrogen. For convenience, the term cycloaliphatic functionality is defined herein to encompass a wide range of functional groups such as alkyl groups, alkenyl groups, alkynyl groups, haloalkyl groups, conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. A cycloaliphatic functionality may comprise one or more halogen atoms which may be the same or different. Exemplary cycloaliphatic functionalities comprise cyclopropyl, cyclobutyl, 1,1,4,4-tetramethylcyclobutyl, piperidinyl, 2,2,6,6-tetramethylpiperydinyl, cyclohexyl and cyclopentyl.

As used herein, the term "aromatic functionality" refers to an array of atoms having a valence of at least one comprising at least one aromatic group. The array of atoms having a valence of at least one, comprising at least one aromatic group, may include heteroatoms such as nitrogen, sulfur, selenium, silicon and oxygen, or may be composed exclusively of carbon and hydrogen. As used herein, the term aromatic functionality includes but is not limited to, phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component ($CH_2)_4$. For convenience, the term aromatic functionality is defined herein to encompass a wide range of functional groups such as alkyl groups, haloalkyl groups, haloaromatic groups, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group, which is an alkyl group. Similarly, the 2-nitrophenyl group is a $C_6$ aromatic functionality comprising a nitro group, wherein the nitro group is a functional group. Aromatic functionalities include halogenated aromatic functionalities. Exemplary aromatic functionalities include, but are not limited to, phenyl, 4-trifluoromethylphenyl, 4-chloromethylphen-1-yl, 3-trichloromethylphen-1-yl (3-CCl$_3$Ph-), 4-(3-bromoprop-1-yl)phen-1-yl (4-BrCH$_2$CH$_2$CH$_2$Ph-), 4-aminophen-1-yl (4-H$_2$NPh-), 4-hydroxymethylphen-1-yl (4-HOCH$_2$Ph-), 4-methylthiophen-1-yl (4-CH$_3$SPh-), 3-methoxyphen-1-yl and 2-nitromethylphen-1-yl (2-NO$_2$CH$_2$Ph), and naphthyl.

As used herein the term "aliphatic functionality" refers to a linear or branched array of atoms that is not cyclic and has a valence of at least one. Aliphatic functionalities are defined to comprise at least one carbon atom. The array of atoms may include heteroatoms such as nitrogen, sulfur, silicon, selenium and oxygen or may be composed exclusively of carbon and hydrogen. For convenience, the term aliphatic functionality is defined herein to encompass, as part of the "linear or branched array of atoms which is not cyclic" a wide range of functional groups such as alkyl groups, haloalkyl groups, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group, which is an alkyl group. Similarly, the 4-nitrobut-1-yl group is a $C_4$ aliphatic functionality comprising a nitro group, wherein the nitro group is a functional group. An aliphatic functionality may be a haloalkyl group which comprises one or more halogen atoms which may be the same or different. Exemplary aliphatic functionalities include, but are not limited to, methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., CH$_2$OH), mercaptomethyl (CH$_2$SH), methylthio (SCH$_3$), methylthiomethyl (CH$_2$SCH$_3$), methoxy, methoxycarbonyl (CH$_3$OCO), nitromethyl (CH$_2$NO$_2$) and thiocarbonyl.

Various structural possibilities exist for the benzoxazole and benzothiazole compounds of Formula (I). In one embodiment, $R^1$ is selected from the group consisting of an aliphatic functionality having 1 to 6 carbons, an aromatic functionality having 6 to 10 carbons, and a cycloaliphatic functionality having 4 to 8 carbons; $R^2$ and $R^3$ are independently selected from the group consisting of a hydroxyl group, a halogen atom, an aliphatic functionality having 1 to 6 carbons, an aromatic functionality having 6 to 10 carbons, and a cycloaliphatic functionality having 4 to 8 carbons; Y is either an oxygen atom or a sulfur atom; "n" has a value of 0 to 4; and "m" has a value of 0 to 3.

In another embodiment, $R^1$ is selected from the group consisting of an aliphatic functionality having 1 to 4 carbons, an aromatic functionality having 6 to 10 carbons, and a cycloaliphatic functionality having 6 to 7 carbons; $R^2$ and $R^3$ are independently selected from the group consisting of a hydroxyl group, a halogen atom, an aliphatic functionality having 1 to 4 carbons, an aromatic functionality having 6 to 10 carbons, and a cycloaliphatic functionality having 6 to 7 carbons; Y is an oxygen atom; "n" has a value of 0 to 4; and "m" has a value of 0 to 3.

In yet another embodiment, $R^1$ is selected from the group consisting of an aliphatic functionality having 1 to 4 carbons, an aromatic functionality having 6 to 10 carbons, and a cycloaliphatic functionality having 6 to 7 carbons; $R^2$ and $R^3$ are independently selected from the group consisting of a hydroxyl group, a halogen atom, an aliphatic functionality having 1 to 4 carbons, an aromatic functionality having 6 to 10 carbons, and a cycloaliphatic functionality having 6 to 8 carbons; Y is a sulfur atom; "n" has a value of 0 to 4; and "m" has a value of 0 to 3.

In specific embodiments, the benzoxazole family of compounds includes the compound 2-(2'-hydroxy-5'-naphthylamidophenyl)benzoxazole having Formula (II), 1-(3-benzoxazol-2-yl-4-hydroxy-phenyl)-3-phenyl urea having Formula (III), 2-(2'-hydroxy-5'-acetamido-phenyl)benzoxazole having Formula (IV), and 2-(2'-hydroxy-5'-phenylamido-phenyl)benzoxazole having Formula (V):

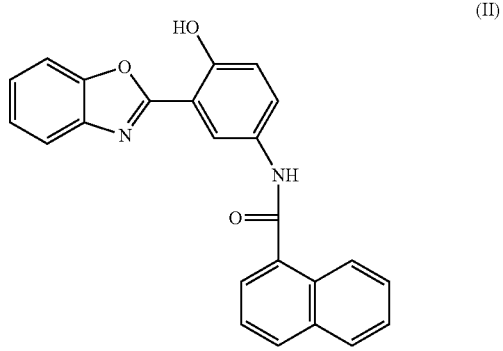

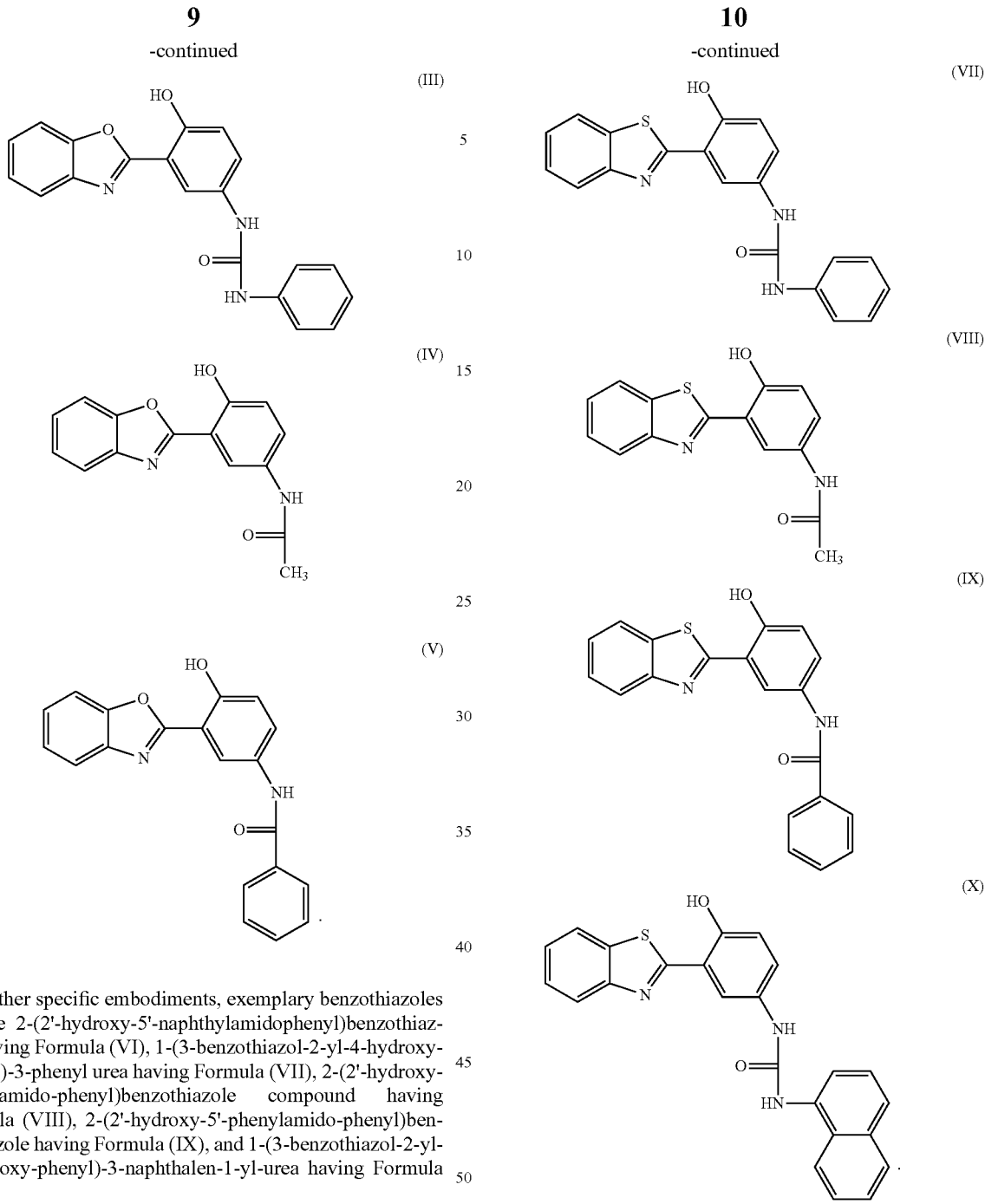

In other specific embodiments, exemplary benzothiazoles include 2-(2'-hydroxy-5'-naphthylamidophenyl)benzothiazole having Formula (VI), 1-(3-benzothiazol-2-yl-4-hydroxyphenyl)-3-phenyl urea having Formula (VII), 2-(2'-hydroxy-5'-acetamido-phenyl)benzothiazole compound having Formula (VIII), 2-(2'-hydroxy-5'-phenylamido-phenyl)benzothiazole having Formula (IX), and 1-(3-benzothiazol-2-yl-4-hydroxy-phenyl)-3-naphthalen-1-yl-urea having Formula (X):

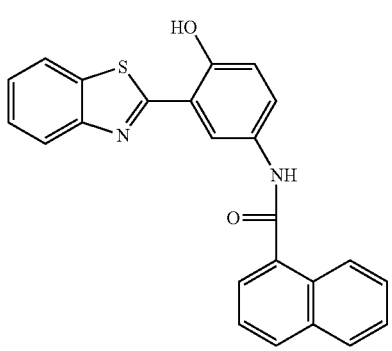

In an embodiment, the article may further comprise a second compound of Formula (I). The first and second compound of Formula (I) can be the same or different. In an embodiment, the first and second compound of Formula (I) are different. For example, the article may have two or more compounds of Formula (I), wherein in one compound of Formula (I) $R^1$ is selected from the group consisting of an aliphatic functionality having 1 to 4 carbons, an aromatic functionality having 6 to 10 carbons, and a cycloaliphatic functionality having 6 to 7 carbons; $R^2$ and $R^3$ are independently selected from the group consisting of a hydroxyl group, a halogen atom, an aliphatic functionality having 1 to 4 carbons, an aromatic functionality having 6 to 10 carbons, and a cycloaliphatic functionality having 6 to 8 carbons; Y is a sulfur atom; "n" has a value of 0 to 4; and "m" has a value of 0 to 3, and in another compound of Formula (I) $R^1$ is selected from the group consisting of an aliphatic functionality having 1 to 4 carbons, an aromatic functionality having 6 to 10 carbons, and a cycloaliphatic functionality having 6 to 7 carbons; $R^2$ and $R^3$ are independently selected from the group consisting of a hydroxyl group, a halogen atom, an aliphatic functionality having 1 to 4 carbons, an aromatic functionality having 6 to 10 carbons, and a cycloaliphatic functionality having 6 to 7 carbons; Y is an oxygen atom; "n" has a value of 0 to 4; and "m" has a value of 0 to 3. In another embodiment, one compound of Formula (I) can be Formula (II), while another compound of Formula (I) can be Formula (III). Other combinations of two or more compounds of Formula (I) are also possible.

The compounds of Formula (I) can be prepared as follows. An amine compound of Formula (XI) is first reacted with a nitro compound of Formula (XII) in the presence of a solvent, an oxidizing agent, and an organic acid to provide an intermediate nitro benzoxazole compound or nitro benzothiazole compound of Formula (XIII):

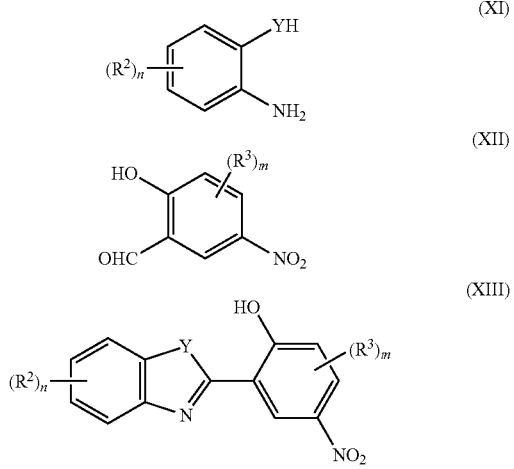

wherein $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3. The benzoxazole or benzothiazole compound of Formula (I) can be obtained by methods known in the art, such as for example, the method disclosed in U.S. Pat. No. 3,164,603, which is herein incorporated in its entirety.

Suitable non-limiting examples of the compound of Formula (XI) include 2-aminophenol, 2-aminothiophenol, 2-amino-4,6-dichlorophenol, 2,3-diaminophenol, 2-amino-4-nitrophenol, and 2,4-diaminophenol. In one embodiment, the compound of Formula (XI) comprises 2-aminophenol or 2-aminothiophenol.

Suitable non-limiting examples of the compound of Formula (XII) include 2-hydroxy-5-nitrosalicylaldehyde, 3-methoxy-5-nitrosalicylaldehyde, 3,5-dinitrosalicylaldehyde, 5-nitrosalicylaldehyde, 4-diethylaminosalicylaldehyde, 5-halo-4-diethylaminosalicylaldehyde, and 5-nitro-4-diethylaminosalicylaldehyde. In one embodiment, the compound of Formula (XII) comprises 5-nitrosalicylaldehyde.

In one embodiment, the amount of the nitro compound of Formula (XII) employed is about 0.75 moles to about 4.0 moles, based on the amount of the amine compound of Formula (XI) employed. Within this range the amount of the nitro compound of Formula (XII) employed is greater than or equal to about 1.0 mole, or more specifically greater than or equal to about 1.5 moles, based on the amount of the amine compound of Formula (XI) employed. Also within this range the amount of the nitro compound of Formula (XII) employed is less than or equal to about 3.5 moles, or more specifically less than or equal to about 3.0 moles, based on the amount of the amine compound of Formula (XI) employed.

Phosphoric acid esters can be used as the solvent in the preparation of the nitro benzoxazole or nitro benzothiazole compounds of Formula (XIII). In one embodiment, the solvent comprises an aliphatic or aromatic phosphoric acid ester. Combinations of the aliphatic and the aromatic phosphoric acid esters can also be used. Specific non-limiting examples of suitable solvents include triethyl phosphate, trimethyl phosphate, tributyl phosphate, tripentyl phosphate, triphenyl phosphate, tricresyl phosphate, trinaphthyl phosphate, cresyldiphenyl phosphate, xylenyldiphenyl phosphate, diphenylisodecyl phosphate, phenyldicresyl phosphate, butyl diphenyl phosphate, 2-ethylhexyldiphenyl phosphate, and a combination of two or more of the foregoing. In one embodiment, the solvent comprises triethyl phosphate.

The amount of solvent that can be used in the synthesis depends on the amount of the amine compound of Formula (XI). In an embodiment, about 750 grams to about 2000 grams of the solvent, based on the amount of the amine compound of Formula (XI) employed. Within this range the amount of the solvent employed is greater than or equal to about 1000 grams, or more specifically greater than or equal to about 1250 grams, based on the amount of the amine compound of Formula (XI) employed. Also within this range the amount of the solvent employed is less than or equal to about 1750 grams, or more specifically less than or equal to about 1500 grams, based on the amount of the amine compound of Formula (XI) employed.

In one embodiment, the oxidizing agent comprises lead tetraacetate, potassium permanganate, copper compounds, manganese compounds, chromium compounds, or a combination of two or more of the foregoing oxidizing agents. Suitable non-limiting examples of copper compounds include cupric acetate, cupric iodide, cupric chloride, cuprous chloride, cupric bromide, cupric iodide, copper sulfate, cupric formate, and a combination of two or more of the foregoing copper compounds. Suitable non-limiting examples of manganese compounds include manganese sulfate, manganese nitrate, manganese dioxide, manganese acetate, manganese trioxide, manganese tetraoxide, manganese naphthenate, barium manganate, and a combination of two or more of the foregoing manganese compounds. Suitable non-limiting examples of chromium compounds include ammonium dichromate, ammonium chromate, barium chromate, calcium dichromate, calcium chromate, chromium nitrate, chromium trihydroxide, chromium oxides, chromium sulfates, lead chromate, lithium chromate, magnesium chromate, potassium chromate, potassium dichromate, potassium tetrachromate, sodium chromate, sodium dichromate, zinc chromate oxide, zinc potassium chromate, and a combination of two or more of the foregoing chromium compounds.

In one embodiment, the amount of the oxidizing agent used ranges from about 0.8 moles to about 2.0 moles, based on the moles of the amine compound of Formula (XI) employed. Within this range the amount of the oxidizing agent employed is greater than or equal to about 1.0 mole, or more specifically greater than or equal to about 1.25 moles, based on the moles of the amine compound of Formula (XI) employed. Also within this range the amount of the oxidizing agent employed is less than or equal to about 1.75 moles, or more specifically less than or equal to about 1.5 moles, based on the moles of the amine compound of Formula (XI) employed.

An organic acid is generally used as a solvent in combination with the phosphoric acid ester solvent to facilitate the reaction to form the nitro benzoxazole or nitro benzothiazole compound of Formula (XIII). Suitable non-limiting examples of the organic acid include glacial acetic acid, formic acid, propionic acid, butanoic acid, methanesulfonic acid, p-toluenesulfonic acid, and ethanesulfonic acid. Typically, the amount of organic acid used in the reaction is equal to the amount of the phosphoric acid ester solvent used as discussed above.

The reaction of the amine compound of Formula (XI) with the nitro compound of Formula (XII) is carried out at a temperature of about 30° C. to about 100° C. Within this range the reaction is carried out at a temperature of greater than or equal to about 40° C., or more specifically at a temperature of greater than or equal to about 50° C. Also within this range the reaction is carried out at a temperature of less than or equal to about 80° C., or more specifically less than or equal to about 60° C. In one embodiment, the time required for the completion of the reaction is from about 5 minutes to about 30 minutes. Within this range the time required for the completion of the reaction is greater than or equal to about 10 minutes, or more specifically greater than or equal to about 15 minutes. Also within this range the time required for the completion of the reaction is less than or equal to about 25 minutes, or more specifically less than or equal to about 20 minutes.

The second step comprises reducing the nitro benzoxazole or nitro benzothiazole compound of Formula (XIII) to produce an amino compound of Formula (XIV):

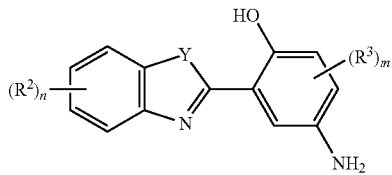

(XIV)

wherein $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3.

The nitro benzoxazole or nitro benzothiazole compound of Formula (XIII) can be reduced to the corresponding amino compound of Formula (XIV) using reduction techniques known to one skilled in the art. In various embodiments, the nitro benzoxazole or nitro benzothiazole compound of Formula (XIII) can be reduced by reacting it with hydrogen in the presence of palladium supported on carbon or other suitable inert supports, such as for example, silica and alumina, a metal/acid system, such as for example, iron/hydrochloric acid, iron/glacial acetic acid, zinc/hydrochloric acid, zinc/glacial acetic acid, tin/hydrochloric acid, or tin/glacial acetic acid; hydrazine hydrate in the presence of ferrous sulfite, or hydrazine hydrate in the presence of palladium supported on carbon or other suitable inert support. A solvent can also be used in the reduction step. Suitable non-limiting examples of solvents include tetrahydrofuran, dichloromethane, chlorobenzene, dimethylformamide, and combinations of two or more of the foregoing solvents. In embodiments where a metal/acid reducing agent is employed, the acid component can also serve as the solvent.

In various embodiments, when the reduction of the nitro benzoxazole or nitro benzothiazole compound of Formula (XIII) is carried out using a metal/acid reducing agent, the amount of metal used ranges from about 6 moles to about 12 moles, based on the moles of the nitro benzoxazole or nitro benzothiazole compound of Formula (XIII) employed. Within this range the amount of the metal employed is greater than or equal to about 7 moles, or more specifically greater than or equal to about 8 moles, based on the moles of the nitro benzoxazole or nitro benzothiazole compound of Formula (XIII) employed. Also within this range the amount of the metal employed is less than or equal to about 11 moles, or more specifically less than or equal to about 10 moles, based on the moles of the nitro benzoxazole or nitro benzothiazole compound of Formula (XIII) employed.

In certain embodiments, where the acid component of the metal/acid reducing agent also serves as the solvent, the amount of the acid used can be about 12 moles to about 60 moles, based on the moles of the nitro benzoxazole or nitro benzothiazole compound of Formula (XIII) employed. Within this range the amount of the acid employed is greater than or equal to about 15 moles, or more specifically greater than or equal to about 20 moles, based on the moles of the nitro benzoxazole or nitro benzothiazole compound of Formula (XIII) employed. Also within this range the amount of the acid employed is less than or equal to about 35 moles, or more specifically less than or equal to about 30 moles, based on the moles of the nitro benzoxazole or nitro benzothiazole compound of Formula (XIII) employed. In certain embodiments, where a solvent is used in addition to the acid component, the amount of the acid employed can be about 6 moles to about 20 moles, based on the moles of the nitro benzoxazole or nitro benzothiazole compound of Formula (XIII) employed. Within this range the amount of the acid employed is greater than or equal to about 10 moles, or more specifically greater than or equal to about 12 moles, based on the moles of the nitro benzoxazole or nitro benzothiazole compound of Formula (XIII) employed. Also within this range the amount of the acid employed is less than or equal to about 18 moles, or more specifically less than or equal to about 15 moles, based on the moles of the nitro benzoxazole or nitro benzothiazole compound of Formula (XIII) employed. The amount of the solvent employed can be about 10 moles to about 40 moles, based on the moles of the nitro benzoxazole or nitro benzothiazole compound of Formula (XIII) employed. Within this range the amount of the solvent employed is greater than or equal to about 15 moles, or more specifically greater than or equal to about 20 moles, based on the moles of the nitro benzoxazole or nitro benzothiazole compound of Formula (XIII) employed. Also within this range the amount of the solvent employed is less than or equal to about 35 moles, or more specifically less than or equal to about 30 moles, based on the moles of the nitro benzoxazole or nitro benzothiazole compound of Formula (XIII) employed.

The reduction of the nitro benzoxazole or nitro benzothiazole compound of Formula (XIII) can be carried out at a temperature from about 50° C. to about 120° C. Within this range the temperature may be greater than or equal to about 60° C., or more specifically greater than or equal to about 75° C. Also within this range the temperature may be less than or equal to about 110° C., or more specifically less than or equal to about 100° C. The time taken to reduce the nitro benzoxazole or nitro benzothiazole compound of Formula (XIII) may be about 0.5 hours to about 2 hours. Within this range the time taken may be greater than or equal to about 0.75 hours, or more specifically greater than or equal to about 1 hour. Also within this range the time taken may be less than or equal to about 1.75 hours, or more specifically less than or equal to about 1.5 hours.

The third step comprises reacting the amino compound of Formula (XIV) with a compound of Formula (XV) or a compound of Formula (XVI):

in the presence of an organic base to provide the compound of Formula (I), wherein $R^1$ is selected from the group consisting of an aliphatic functionality having 1 to 12 carbons, an aromatic functionality having 3 to 20 carbons, and a cycloaliphatic functionality having 3 to 20 carbons; and $R^4$ is a halogen atom.

Suitable non-limiting examples of the compound of Formula (XV) include acetyl chloride, 1-naphthoyl chloride, 2-naphthoyl chloride, 4-methylbenzoyl chloride, 2-methylbenzoyl chloride, 2-methoxybenzoyl chloride, 4-methoxybenzoyl chloride, 4-hydroxybenzoyl chloride, 4,4-dimethylaminobenzoyl chloride, terephthaloyl chloride, isophthaloyl chloride, and biphenyl-4-carbonyl chloride. Suitable non-limiting examples of the compound of Formula (XVI) include methyl isocyanate, phenyl isocyanate, ethyl isocyanate, propyl isocyanate, and butyl isocyanate. In one embodiment, the compound of Formula (XV) comprises 1-naphthoyl chloride and the compound of Formula (XVI) comprises phenyl isocyanate.

In one embodiment, the amount of compound of Formula (XV) or Formula (XVI) employed is about 0.5 moles to about 1.5 moles, based on the moles of the amino compound of Formula (XIV) employed. Within this range the amount of compound of Formula (XV) or Formula (XVI) employed is greater than or equal to about 0.75 moles, or more specifically greater than or equal to about 0.95 moles, based on the moles of the amino compound of Formula (XIV) employed. Also within this range the amount of compound of Formula (XV) or Formula (XVI) employed is less than or equal to about 1.25 moles, or more specifically less than or equal to about 1.0 mole based on the moles of the amino compound of Formula (XIV) employed.

A tertiary amine is generally used as the organic base in the third step. Some non-limiting examples of organic bases include triethylamine, piperidine, pyridine, pyrrolidone, N,N-dimethylaminopyridine, N,N-diisopropylamine, N-methylpiperidine, and morpholine.

The organic base can be used in an amount from about 10 moles to about 70 moles, based on the moles of the amino compound of Formula (XIV). Within this range the amount of the organic base employed is greater than or equal to about 20 moles, or more specifically greater than or equal to about 40 moles, based on the moles of the amino compound of Formula (XIV) employed. Also within this range the amount of the organic base employed is less than or equal to about 60 moles, or more specifically less than or equal to about 50 moles, based on the moles of the amino compound of Formula (XIV) employed.

The third step is carried out at a temperature of about 0° C. to about 70° C. Within this range the reaction is carried out at a temperature greater than or equal to about 10° C., or more specifically greater than or equal to about 30° C. Also within this range the reaction is carried out at a temperature less than or equal to about 50° C., or more specifically less than or equal to about 40° C. The third step generally requires about 5 minutes to about 60 minutes for complete reaction. Within this range the time required for complete reaction may be greater than or equal to 15 minutes, or more specifically greater than or equal to about 20 minutes. Also within this range the time required for complete reaction may be less than or equal to about 50 minutes, or less than or equal to about 40 minutes.

In one embodiment, a method of making an article comprises providing an authenticatable polymer composition, and forming an article from the authenticatable polymer composition. The authenticatable polymer composition is provided by incorporating the authentication compound of Formula (I) in a polymer. Any thermoplastic polymer known in the art can be used as the polymer. Non-limiting examples of thermoplastic polymers include polystyrene, poly(methyl methacrylate) (PMMA), poly(vinyl chloride) (PVC), acrylonitrile-butadiene-styrene copolymer (ABS), acrylonitrile-styrene-acrylate copolymer (ASA), styrene-acrylonitrile copolymer (SAN), polycarbonate, poly(phenyleneoxide), polyolefins, such as polypropylene and polyethylene, poly(acrylonitrile), polyamide, polyacetal, polyesters such as poly(ethyleneterephthalate) and poly(butyleneterephthalate), polyetherimides, such as ULTEM™ polyetherimide, and any mixture of the foregoing thermoplastic polymers. Further, the authenticatable polymer compositions can comprise one or more thermoset polymers. Non-limiting examples of thermoset polymers include phenolic resins, urea resins, melamine resins, unsaturated polyester resins, epoxy resins and poly(diallylphthalate) resins. Polycarbonates are particularly valuable thermoplastic polymers for producing authenticatable polymer compositions and authenticatable articles since they have excellent transparency and desirable mechanical properties. A suitable example of a polycarbonate is bisphenol A polycarbonate, which is widely available commercially.

In addition to the authentication compound of Formula (I), the polymer compositions described herein may also comprise other additives, such as for example pigments and dyes, filler materials, stabilizers, mold release agents, processing aids, flame retardants, drip retardants, nucleating agents, UV blockers, dyes, pigments, particulate, conductive fillers, such as for example conductive carbon black, and carbon nanotubes, reinforcing fillers, antioxidants, anti-static agents and blowing agents. The additives used should be such that they do not interfere with the authenticating capabilities of the authentication compound of Formula (I).

The authenticatable polymer compositions are generally obtained by blending the authentication compound of Formula (I) with one or more polymers in a suitable manner, and subjecting the resulting blend to a molding step using known techniques such as injection molding, extrusion, and melt-spinning. The polymer precursors for the polymer can be premixed with a pulverized authentication compound of Formula (I) in a suitable mixer. The polymer used can be in a pellet, powder, and/or liquid form. The resulting mixture is then treated in a kneader, roller mill, Banbury™ mixer or an extruder to disperse or dissolve the authentication compound of Formula (I) in the polymer. The authentication compounds of Formula (I) can be incorporated into the polymer such that they are uniformly dispersed throughout the authenticatable polymer, or they are dispersed on a portion of the authenticatable polymer. In various embodiments the authentication compound of Formula (I) may be dispersed on a portion of the polymer by coating, molding, or by welding a portion of another polymer comprising an authentication compound on the polymer. In one embodiment, the authentication compound of Formula (I) may be introduced using a concentrate (for example, a master-batch) either during the polymer compounding stage or during the stage of forming the article.

The use of the authenticatable polymer compositions disclosed herein in various polymer based articles allows for one or more parties at any point along the manufacturing chain, distribution chain, point of sale or point of use of the article to confirm or identify the presence or absence of the disclosed composition in the authenticatable polymer composition or authenticatable article. In one embodiment, there is provided a method of authenticating that an article is an authenticatable article by identifying the presence of a specific authenticatable compound in the article. The presence of the authenticatable compound in the article can be determined by known analytical methods, such as by an ultraviolet or visible light detector, as further described below.

The authentication compound of Formula (I) is added to the polymer in an amount sufficient to be detected by an analytical method as discussed below. When a detector other than the human eye is used, it is preferred to have a signal to noise ratio greater than or equal to about 5, more specifically greater than about 20, and even more specifically greater than about 50. Thus when a detector that is considerably more sensitive than the human eye is used, the concentration of the authentication compound of Formula (I) in the authenticatable polymer composition can be such that the color change resulting from exposing the authenticatable polymer composition to an excitation stimulus may not be apparent to the unaided human eye. As used herein, the phrase "signal to noise ratio" refers to the measure of the signal strength relative to the background noise. In one embodiment, the authentication compound of Formula (I) may be present in the polymer in an amount ranging from about $1\times10^{-7}$ percent by weight to about 10 percent by weight, based on the weight of the polymer. Within this range the amount of authentication compound of Formula (I) is greater than or equal to about 0.1 percent by weight, more specifically greater than or equal to about 0.2 percent by weight, based on the weight of the polymer. Also within this range the amount of authentication compound of Formula (I) is less than or equal to 5 percent by weight, or more specifically less than or equal to 2 percent by weight, based on the weight of the polymer.

In another embodiment, a method for ensuring the authenticity of an article is provided. The method comprises identifying the presence of an authentication compound of Formula (I) in the article. The method of authenticating comprises subjecting the article to an excitation stimulus and then measuring the resulting response obtained using a detector.

In one embodiment, the excitation stimulus has a wavelength ranging from about 250 nm to about 450 nm. Within this range the excitation stimulus has a wavelength ranging from greater than or equal to about 275 nm, or more specifically greater than or equal to about 335 nm. Also within this range the excitation stimulus has a wavelength ranging from less than or equal to about 440 nm, or more specifically less than or equal to about 435 nm. Suitable examples of excitation stimulus include an ultraviolet-visible (UV-Visible) lamp, a light emitting diode (LED), a laser diode, a combination of at least two LEDs, a combination of an ultraviolet radiation source and a white LED (UV LED), and a combination of any of the foregoing. In one embodiment, a UV-Visible lamp at a wavelength of about 340 nm to about 390 nm is employed as the excitation stimulus. In another embodiment, the excitation stimulus is a LED with a peak wavelength located between about 350 nm and about 435 nm. In one specific embodiment, the stimulus is a LED with a peak at about 380 nm. Several light sources (such as LEDs) can be used separately to generate an optical response. In one embodiment, a white LED and a UV LED is used instead of single source. In another embodiment a white LED, a UV LED and a blue LED is used because it allows for an easier distinction between long Stokes shift fluorophores and counterfeits using regular fluorophores.

When an article containing the authentication compound of Formula (I) is subjected to the excitation stimulus, the authentication compound contained in the article gives out a signal. As used herein the term "signal" refers to a response detectable by an analytical method, such as for example vibrational spectroscopy, fluorescence spectroscopy, luminescence spectroscopy, electronic spectroscopy and combinations of analytical methods thereof. This signal is characteristic of the authentication compound of Formula (I) and is hereinafter referred to as the signature signal.

The signature signal emitted from the stimulated portion of the authenticatable article is measured with a detector. The signature signal is characteristic of the authentication compound of Formula (I) present in the authenticated article. Generally the detector employed comprises a photodetector that can detect the change in wavelength and intensity of the signature signal as compared to the excitation stimulus.

In one embodiment, the detector employed is capable of detecting the signature signal having a peak wavelength of about 400 nm to about 700 nm. Within this range the detector employed is capable of detecting the signature signal having a peak wavelength ranging from greater than or equal to about 450 nm, or more specifically greater than or equal to about 470 nm. Also within this range the detector employed is capable of detecting the signature signal having a peak wavelength ranging from less than or equal to about 650 nm, or more specifically less than or equal to about 600 nm In one embodiment, the step of measuring the response of the authenticatable article with a photodetector comprises measuring the resultant fluorescence. The fluorescence may be measured in the transmission mode, reflectance mode or in the emission mode. In one embodiment, the fluorescence is measured in the reflectance mode.

When a compound that is capable of fluorescing is irradiated with an excitation stimulus, the fluorescence radiation emitted by the compound generally has a wavelength that is higher than that of the excitation stimulus. The difference between the wavelength of the excitation stimulus and the wavelength of the emitted light is called Stokes shift. Typically the fluorescence radiation obtained as a signature signal from the authenticated article has a peak wavelength in a range of about 450 nm to about 650 nm. Within this range the peak wavelength of the signature signal is greater than or equal to about 460 nm, or more specifically greater than or equal to about 470 nm. Also within this range the peak wavelength of the signature signal is less than or equal to about 600 nm, or more specifically less than or equal to about 550 nm. The peak wavelength of the fluorescence radiation is hereinafter at times referred to as fluorescence emission maximum. Generally, a long Stokes shift results when the excitation stimulus wavelength is at about 250 nm to about 400 nm, and the fluorescence emission wavelength is at greater than or equal to about 450 nm. As used herein, an observed Stokes shift is considered to be a "long Stokes shift" when the difference between the excitation stimulus wavelength and the emission wavelength is greater than or equal to 50 nm, more specifically greater than or equal to about 150 nm. The compounds of Formula (I) typically have long Stokes shifts that are generally greater than about 150 nm.

The authenticatable polymer compositions comprising the authentication compound of Formula (I) may be used for any application in which the physical and chemical properties of the base polymer or a combination of the base polymer with other additives are desired for the desired end-use. In one embodiment, the authenticatable polymer compositions are used to make formed articles such as data storage media. In one exemplary embodiment, the authenticatable polymers will be used to make data storage media such as compact discs (CDs) and digital video discs (DVDs). Other embodiments include packaging material (and especially drug packaging), automotive parts such as lenses, telecom accessories (such as cell phone covers), computers and consumer electronics, construction materials, medical devices, eyewear products, secure documents including passports and identification (ID) cards, credit cards, films, and sheets (including those used in display applications).

After the authenticatable polymer composition has been produced, it may be formed into a data storage media using various known molding techniques, processing techniques, or combinations thereof. Possible molding techniques include injection molding, film casting, extrusion, press molding, blow molding, and stamping. One possible process comprises an injection molding-compression technique where a mold is filled with a molten polymer. The mold used may contain a preform, inserts and fillers. The authenticatable polymer is cooled and, while still in an at least partially molten state, compressed to imprint the desired surface features, such as for example, pits, grooves, edge features, and smoothness, arranged in spiral concentric or other orientation, onto the desired portion(s) of the formed part. The imprints can be made on either one side or on both sides in the desired areas. The formed part is then cooled to room temperature. Once the formed part has been produced, additional processing, such as electroplating, coating techniques (including for example spin coating, spray coating, vapor deposition, screen printing, painting, and dipping), lamination, sputtering, and combinations comprising a of the foregoing processing techniques, among others known in the art, may be employed to dispose desired layers on the substrate.

A further understanding of the techniques described above can be obtained by reference to certain specific examples that are provided herein for purposes of illustration only and are not intended to be limiting.

EXAMPLES

5-Nitrosalicylaldehyde, 2-aminothiophenol, lead tetraacetate, phenyl isocyanate, and naphthoyl chloride used in the synthesis of the benzothiazoles and/or the benzoxazoles were procured from Aldrich Chemicals, U.S.A.; and glacial acetic acid and 2-aminophenol were procured from S.D. Fine Chemicals, India. Bisphenol A homopolycarbonate (having a molecular weight of about 43000 based on polystyrene standards) was obtained from GE Plastics. All other reagents were procured from Aldrich Chemicals, U.S.A.

Proton NMR spectra were measured using a 300 megahertz Bruker NMR spectrometer using dimethyl sulfoxide (DMSO)-$d_6$ as the solvent. The sample for the analysis was prepared generally by dissolving about 10 to 15 milligrams (mg) of the product in 0.5 milliliters (ml) of DMSO-$d_6$.

The benzothiazole and benzoxazole products were further characterized by using a liquid chromatograph-mass spectrometer (LC-MS) system comprising an Alliance Systems liquid chromatograph equipped with an Xterra C18 column having a length of 50 millimeters (mm), a diameter of 4.6 mm, and a column packing having a pore size of 5 microns, with the column output coupled with a Quattro Ultima Pt mass spectrometer. The analysis sample was prepared by dissolving about 20 mg of the product in 5 ml of dimethylformamide and further diluting with 20 ml of acetonitrile. The eluent was a 80:20 volume/volume mixture of water and acetonitrile containing 0.05 weight percent of formic acid. A flow rate of 1.0 ml per minute (ml/minute) of the eluent and a column temperature of 30° C. was employed for separating the components. The eluted product and other components were characterized by mass spectrometry. A plot of mass to charge ratio (m/z) versus the percentage molecular ion abundance led to the identification of the desired benzoxazole or benzothiazole compound as the molecular ion with the highest relative abundance.

UV-Visible absorbance was measured using a double beam Perkin-Elmer Lambda 900 UV-VIS-NIR spectrophotometer. About 0.00005 moles of the benzoxazole or benzothiazole compound was dissolved in 100 ml of dimethylformamide to obtain a stock solution. A 5 ml portion of the stock solution was further diluted to 50 ml using dimethylformamide and utilized for the absorption measurements. The measurement was made in the absorption mode of the instrument over a wavelength range from 200 nm to 700 nm.

Fluorescence emission spectra of the benzoxazole and benzothiazole compounds were recorded using a Hitachi F-4500 spectrophotometer at an excitation radiation having a wavelength of 365 nm. Measurements were made on 1-millimeter thick bisphenol A homopolycarbonate molded chips having 0.0005 weight percent of the sample. A mirror was used as the reflective background to measure the fluorescence emission.

Thermogravimetric analysis (also referred to as "TGA") was carried out using a TGA 2950 instrument equipped with an auto sampler, and available from TA Instruments. TGA measures the amount of weight change in a material as a function of temperature in a controlled atmosphere. TGA can be carried out either using a programmed temperature setting whereby the sample is heated at a pre-determined rate, or the sample is subjected to a constant temperature (isothermal condition). In the present disclosure the sample was equilibrated to an initial temperature of 40° C. for a period of 2 to 3 minutes and then heated at the rate of 10° C. per minute up to a maximum temperature of 600° C. under air. The weight of the sample was monitored continuously throughout the heating process. Any weight loss is generally indicative of decomposition or degradation of the sample. This technique was used to measure the thermal stability for the benzoxazole and benzothiazole compounds disclosed herein. The thermal stability data in turn was used to identify benzoxazole and benzothiazole compounds that can be beneficially used in polymer resin compositions prepared by polymer processing techniques. A weight loss temperature curve can be generated from the TGA experiment. The TGA results are expressed in terms of $T_d$. For the purposes of this disclosure, $T_d$ of a sample represents the inflection point on the weight loss temperature curve when the sample undergoes a weight loss of 10 percent, relative to the initial weight of the sample. In general, the higher the $T_d$ of the benzoxazole or the benzothiazole compound, the higher will be its suitability for high temperature compositions and high temperature end uses.

Example 1 Describes the Preparation of 2-(2'-hydroxy-5'-naphthylamidophenyl)benzoxazole compound (Formula (II))

Step A describes the preparation of 2-(2'-hydroxy-5'-nitrophenyl)benzoxazole. To a 250 ml round-bottomed flask fitted with a stirrer and a temperature indicator were charged 2-aminophenol (2.73 grams (g)) and triethyl phosphate (25 g). The resulting mixture was stirred at 30° C. to form a solution. 5-nitrosalicylaldehyde (5 g) was added with stirring to the solution, and after about 10 minutes, glacial acetic acid (25 g) was added. After stirring for about 15 minutes, lead tetraacetate (15 g) was added, whereby an exotherm was observed. The temperature of the resulting reaction mixture was maintained at about 60° C., and then ethylene glycol (2.5 g) was added to the reaction mixture. After being stirred for about an hour at 60° C., the reaction mixture was cooled to about 30° C., filtered, and the filter cake was washed with about 20 ml of ethanol, then with about 100 ml of water, and dried to give the desired compound in a yield of 5.1 g.

Step B describes the preparation of 2-(2'-hydroxy-5'-aminophenyl)benzoxazole. To a 250 ml round-bottomed flask fitted with a stirrer and a temperature indicator were charged 5 grams of the 2-(2'-hydroxy-5'-nitrophenyl)benzoxazole compound (prepared in Step A), and glacial acetic acid (37.5 ml) to form a mixture. To this mixture was added powdered zinc dust (9.98 g) in small portions over a period of about 30 minutes. An exotherm was observed. The temperature of the reaction mixture was maintained at about 80° C. After about one hour, the reaction mixture was diluted to twice its volume using deionized water, and treated with activated charcoal (0.5 g) and diatomaceous earth (2.5 g). After allowing the temperature of the resulting mixture to drop to about 35° C., the mixture was filtered and the filter cake was washed with 50 ml of 50 percent (volume by volume) acetic acid in water. The filtrate was then cooled to about 10° C., its pH was adjusted to 7.0 using 15 percent aqueous ammonium hydroxide solution, filtered, and the filter cake was dried to give the desired compound in a yield of 3.7 g.

Proton NMR spectrum of the 2-(2'-hydroxy-5'-aminophenyl)benzoxazole compound (prepared in Step B) showed peaks at δ 4.93 (s, 2 protons); 6.84 (m, 2 protons); 7.23 (m, 1 proton); 7.44 (m, 2 protons); 7.83 (m, 2 protons); and 10.40 (m, 1 proton).

Step C describes the preparation of 2-(2'-hydroxy-5'-naphthylamidophenyl)benzoxazole compound (Formula (II)). To a 250 ml round-bottomed flask fitted with a stirrer and a temperature indicator were charged 1 g of the 2-(2'-hydroxy-5'-aminophenyl)benzoxazole compound (prepared in Step B), and 5.8 g of pyridine at 30° C. to form a solution. Naphthoyl chloride (0.92 g) was added to the solution with stirring, and the resulting mixture was heated to 75° C. After being stirred at 75° C. for about 15 minutes, the reaction mixture was filtered, and the filter cake was washed with about 50 ml of water and dried to give the compound of Formula (II) in a yield of 0.68 g.

Proton NMR spectrum of the compound of Formula (II) showed peaks at δ 7.17 (m, 1 proton); 7.48 (m, 2 proton); 7.61 (m, 3 proton); 7.85 (m, 4 proton); 8.08 (m, 2 proton); 8.25 (m, 1 proton); 8.77 (m, 1 proton); 10.68 (s, 1 proton); and 11.11 (s, 1 proton). LC-MS analysis of the compound showed a molecular ion peak (M+) having a mass of 380 amu (atomic mass units). UV-Visible spectrum of the compound in dimethylformamide as a solvent showed an absorbance maximum at 344 nm. The compound had a $T_d$ of 320° C., as measured using the TGA technique described above.

Example 2 Describes the Preparation of 1-(3-benzoxazol-2-yl-4-hydroxy-phenyl)-3-phenyl urea compound (Formula (III))

A solution of 1 gram of the 2-(2'-hydroxy-5'-aminophenyl)benzoxazole compound (prepared in Step B of Example 1), and triethyl phosphate (20 g) was prepared in a 250 ml round-bottomed flask fitted with a stirrer and a temperature indicator. The solution was maintained at a temperature of 30° C. and treated with phenyl isocyanate (0.53 g) with stirring. The resulting reaction mixture was heated to a temperature of 125° C. and maintained for about 15 minutes. Then the reaction mixture was filtered, and the filter cake was washed with about 50 ml of water and dried to give the desired compound of Formula (III) in a yield of 0.95 g.

Proton NMR spectrum of the compound of Formula (III) showed peaks at δ 7.00 (m, 2 protons); 7.27 (m, 2 protons); 7.48 (m, 5 protons); 8.12 (m, 2 protons); 8.40 (s, 1 proton); 8.66 (d, 2 protons); and 11.24 (s, 1 proton). LC-MS analysis of the compound showed a molecular ion peak (M+) having a mass of 345.1 amu. UV-Visible spectrum of the compound in dimethylformamide as a solvent showed an absorbance maximum at 355 nm. The compound had a $T_d$ of 300° C., as measured using the TGA technique described above.

Example 3 Describes the Preparation of 2-(2'-hydroxy-5'-acetamido-phenyl)benzoxazole compound (Formula (IV))

This compound was prepared using the same procedure used in Step C of Example 1 except that 3.0 g of the 2-(2'-hydroxy-5'-aminophenyl)benzoxazole compound (prepared in Step B of Example 1), 17 g of pyridine, and 1.15 g of acetyl chloride were used. The desired compound of Formula (IV) was obtained in a yield of 1.6 g.

Proton NMR spectrum of the compound of Formula (IV) showed peaks at δ 2.04 (s, 3 protons); 7.09 (m, 1 proton); 7.52 (m, 3 protons); 7.86 (d, 2 protons); 8.45 (d, 1 proton); 10.03 (s, 1 proton); and 10.99 (s, 1 proton). LC-MS analysis of the compound showed a molecular ion peak (M+) having a mass of 268.73 amu. UV-Visible spectrum of the compound in dimethylformamide as a solvent showed an absorbance maximum at 348 nm. The compound had a $T_d$ of 295° C., as measured using the TGA technique described above.

Example 4 Describes the Preparation of 2-(2'-hydroxy-5'-phenylamido-phenyl)benzoxazole compound (Formula (V))

This compound was prepared using the same procedure used in Step C of Example 1 except that 1.0 g of the 2-(2'-hydroxy-5'-aminophenyl)benzoxazole compound (prepared in Step B of Example 1), 5.8 g of pyridine, and 0.68 g of benzoyl chloride were used. The desired compound of Formula (V) was obtained in a yield of 0.76 g.

Proton NMR spectrum of the compound of Formula (V) showed peaks at δ 7.15 (m, 1 proton); 7.47 (m, 2 protons); 7.55 (m, 3 protons); 7.86 (m, 3 protons); 8.00 (m, 2 protons); 8.66 (s, 1 proton); 10.38 (s, 1 proton); and 11.05 (s, 1 proton). LC-MS analysis of the compound showed a molecular ion peak (M+) having a mass of 330 amu. UV-Visible spectrum of the compound in dimethylformamide as a solvent showed an absorbance maximum at 345 nm. The compound had a $T_d$ of 300° C., as measured using the TGA technique described above.

Example 5 Describes the Preparation of 2-(2'-hydroxy-5'-naphthylamidophenyl)benzothiazole compound (Formula (VI))

Step A describes the preparation of 2-(2'-hydroxy-5'-nitrophenyl)benzothiazole. To a 250 ml round-bottomed flask fitted with a stirrer and a temperature indicator were charged 2-aminothiophenol (3 g) and triethyl phosphate (24 g). The mixture formed a solution at a temperature of 30° C. Then 5-nitrosalicylaldehyde (4.8 g) was added with stirring, and after about 10 minutes glacial acetic acid (25 g) was added. After being stirred for about 15 minutes, lead tetraacetate (15 g) was added, whereby an exotherm was observed. The temperature of the resulting reaction mixture was maintained at about 60° C. by monitoring the temperature of the oil-bath. After being maintained at this temperature for about 1 hour, the desired compound was isolated by using the procedure described in Step A of Example 1. The desired compound was obtained in a yield of 4.7 g.

Step B describes the preparation of 2-(2'-hydroxy-5'-aminophenyl)benzothiazole. This compound was prepared using the same procedure as described previously for Step B of Example 1 except that 4 g of the 2-(2'-hydroxy-5'-nitrophenyl)benzothiazole compound (prepared in Step A of Example 3), 7.51 g of zinc dust, and 0.3 g of activated charcoal were used. The desired compound was obtained in a yield of 3.0 g.

Proton NMR spectrum of the 2-(2'-hydroxy-5'-aminophenyl)benzothiazole compound (prepared in Step B of Example 5) showed peaks at δ 4.86 (s, 2 protons); 6.78 (m, 2 protons); 7.48 (m, 3 protons); 8.07 (q, 2 protons); and 10.07 (s, 1 proton).

Step C describes the 2-(2'-hydroxy-5'-naphthylamidophenyl)benzothiazole compound (Formula (VI)). This compound was prepared using the same procedure used in Step C of Example 1 except that 1 gram of the 2-(2'-hydroxy-5'-aminophenyl)benzothiazole compound (prepared in Step B of Example 5), 10 g of pyridine and 0.92 g of naphthoyl chloride were used. The desired compound of Formula (VI) was obtained in a yield of 0.67 g.

Proton NMR spectrum of the compound of Formula (VI) showed peaks at δ 7.17 (m, 1 proton); 7.48 (m, 2 protons); 7.63 (m, 3 protons); 7.83 (m, 4 protons); 8.07 (m, 2 protons); 8.26 (m, 1 proton); 8.78 (s, 1 proton); 10.69 (s, 1 proton); and 11.11 (s, 1 proton). LC-MS analysis of the compound showed a molecular ion peak (M+) having a mass of 396 amu. UV-Visible spectrum of the compound in dimethylformamide as a solvent showed an absorbance maximum at 360 nm. The compound had a $T_d$ of 350° C., as measured using the TGA technique described above.

Example 6 Describes the Preparation of 1-(3-benzothiazol-2-yl-4-hydroxy-phenyl)-3-phenyl urea (Formula (VII)).

The procedure to prepare this compound was the same as that described for preparing the compound of Example 5 except that 1 gram of the 2-(2'-hydroxy-5'-aminophenyl)benzothiazole compound (prepared in Step B of Example 5), 18.6 g of triethyl phosphate and 0.55 g of phenyl isocyanate were used. The desired compound of Formula (VII) was obtained in a yield of 0.76 g.

Proton NMR spectrum of the compound of Formula (VII) showed peaks at δ 6.99 (m, 2 proton); 7.28 (m, 2 proton); 7.49 (m, 5 proton); 8.10 (m, 2 protons); 8.41 (s, 1 proton); 8.67 (m, 2 protons); and 11.24 (s, 1 proton). LC-MS analysis of the compound showed a molecular ion peak (M+) having a mass of 361 amu. UV-Visible spectrum of the compound in dimethylformamide as a solvent showed an absorbance maximum at 363 nm. The compound had a $T_d$ of 300° C., as measured using the TGA technique described above.

Example 7 Describes the Preparation of 2-(2'-hydroxy-5'-acetamido-phenyl)benzothiazole compound (Formula (VIII))

This compound was prepared using the same procedure used in Step C of Example 1 except that 2.0 g of the 2-(2'-hydroxy-5'-aminophenyl)benzothiazole compound (prepared in Step B of Example 5), 15 g of pyridine and 0.67 g of acetyl chloride were used. The desired compound of Formula (VIII) was obtained in a yield of 1.6 g.

Proton NMR spectrum of the compound of Formula (VIII) showed peaks at δ 2.11 (s, 3 protons); 7.08 (m, 1 proton); 7.53 (m, 3 protons); 7.87 (m, 2 protons); 8.46 (s, 1 proton); 10.03 (s, 1 proton); and 10.98 (s, 1 proton). LC-MS analysis of the compound showed a molecular ion peak (M+) having a mass of 284 amu. UV-Visible spectrum of the compound in dimethylformamide as a solvent showed an absorbance maximum at 355 nm. The compound had a $T_d$ of 300° C., as measured using the TGA technique described above.

Example 8 Describes the Preparation of 2-(2'-hydroxy-5'-phenylamido-phenyl)benzothiazole (Formula (IX))

This compound was prepared using the same procedure used in Step C of Example 1 except that 1.0 g of the 2-(2'-hydroxy-5'-aminophenyl)benzothiazole compound (prepared in Step B of Example 5), 10.0 g of pyridine and 0.64 g of benzoyl chloride were used. The desired compound of Formula (IX) was obtained in a yield of 0.65 g.

Proton NMR spectrum of the compound of Formula (IX) showed peaks at δ 7.11 (m, 1 proton); 7.47 (m, 1 proton); 7.56 (m, 4 protons); 7.87 (m, 1 proton); 8.05 (m, 3 protons; 8.16 (m, 1 proton); 8.69 (m, 1 proton); 10.33 (s, 1 proton) and 11.44 (s, 1 proton). LC-MS analysis of the compound showed a molecular ion peak (M+) having a mass of 346 amu. UV-Visible spectrum of the compound in dimethylformamide as a solvent showed an absorbance maximum at 353 nm. The compound had a $T_d$ of 330° C., as measured using the TGA technique described above.

Example 9 Describes the Preparation of 1-(3-benzothiazol-2-yl-4-hydroxy-phenyl)-3-naphthalen-1-yl-urea compound (Formula (X))

This compound was prepared using the same procedure used in Example 4 except that 1.0 g of the 2-(2'-hydroxy-5'-aminophenyl)benzothiazole compound (prepared in Step B of Example 5), 20 g of triethyl phosphate and 0.78 g of naphthylisocyanate were used. The desired compound of Formula (X) was obtained in a yield of 1.0 g.

Proton NMR spectrum of the compound of Formula (X) showed peaks at δ 7.06 (m, 1 proton); 7.53 (m, 7 protons); 7.94 (m, 1 proton); 8.05 (m, 2 protons); 8.14 (m, 2 protons); 8.45 (s, 1 proton); 8.72 (s, 1 proton); 8.10 (s, 1 proton); and 11.26 (s, 1 proton). LC-MS analysis of the compound showed a molecular ion peak (M+) having a mass of 411 amu. UV-Visible spectrum of the compound in dimethylformamide as a solvent showed an absorbance maximum at 363 nm. The compound had a $T_d$ of 300° C., as measured using the TGA technique described above.

The general procedure used for preparing extruded polymer samples incorporating the benzoxazole or the benzothiazole compounds described above is as follows. A 1 kilogram sample of bisphenol A homopolycarbonate and about 0.005 weight percent (based on the total weight of the sample) of each of the benzoxazole compound or benzothiazole compounds of Examples 1 to 9 was taken in different polyethylene bags and shaken vigorously for about 3 to 5 minutes. The resultant mixtures were compounded using a Werner and Pfleiderer™ Twin Screw Extruder, Model ZSK-25 Mega Compounder under vacuum under the conditions specified in Table 1 to produce polymer pellets.

TABLE 1

| | |
|---|---|
| Feed zone temperature (° C.) | 128 |
| Zone 1 temperature (° C.) | 280 |
| Zone 2 temperature (° C.) | 285 |
| Zone 3 temperature (° C.) | 285 |
| Zone 4 temperature (° C.) | 290 |
| Throat/Die temperature (° C.) | 290 |
| Screw speed (Revolutions per minute) | 300 |
| Temperature of Melt (° C.) | 300 |
| Torque (Nm) | 58-62 |

The general procedure used for producing molded chips from the extruded pellets prepared as described above is as follows. The extruded pellets were dried in an oven maintained at 120° C. for about 4 hours. Then the dried pellets were subjected to molding using a LTM-Demag molding machine to provided step-chips. Step-chips can be defined as single molded chips having sections of 1, 2 and 3 mm thickness down the length of the chip. The step-chips are useful for weatherability studies. The conditions for preparing the step-chips are shown in Table 2

TABLE 2

| | |
|---|---|
| Feed zone temperature (° C.) | 110 |
| Zone 1 temperature (° C.) | 300 |
| Zone 2 temperature (° C.) | 290 |
| Zone 3 temperature (° C.) | 275 |
| Nozzle Temperature (° C.) | 295 |
| Temperature of Melt (° C.) | 300 |
| Mold temperature (° C.) | 85 |
| Sample drying time (hours) | 4 |
| Sample drying temperature (° C.) | 120 |
| Cycle time (seconds) | 125 |
| Injection time (seconds) | 1.2 |
| Injection speed (revolutions per minute) | 25 |
| Injection pressure (bar) | 50 |
| Screw speed (Revolutions per minute) | 300 |
| Holding pressure (bar) | 40 |
| Holding time (seconds) | 10 |
| Cooling time (seconds) | 15 |

The step-chips were then used to measure the fluorescence emission spectrum displayed by the benzoxazole and the benzothiazole compounds present in the plaque. As shown in Table 3 below the benzoxazole and benzothiazole compounds prepared in Examples 1 to 9 show a UV-Visible absorbance maximum in the ultraviolet range of about 200 nm to about 400 nm and the fluorescence emission maximum in the visible range of about 400 nm to about 800 nm. Further, the compounds shown in Table 3 have a long Stokes shift which is indicated by the greater than 50 nm difference between the absorbance maximum and the emission maximum of the compounds. The benzoxazole and the benzothiazole compounds also show a $T_d$ of greater than 290° C.

TABLE 3

| Example | Compound of Formula | UV-Visible absorbance maximum (nm) | Fluorescence emission maximum (nm) | Stokes shift (nm) | $T_d$ (° C.) |
|---|---|---|---|---|---|
| 1 | II | 344 | 509 | 165 | 320 |
| 2 | III | 360 | 539 | 179 | 300 |
| 3 | IV | 348 | 511 | 163 | 295 |
| 4 | V | 345 | 507 | 162 | 300 |
| 5 | VI | 355 | 507 | 152 | 350 |
| 6 | VII | 363 | 525 | 162 | 300 |
| 7 | VIII | 355 | 541 | 186 | 300 |
| 8 | IX | 353 | 541 | 188 | 330 |
| 9 | X | 363 | 528 | 165 | 300 |

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

The invention claimed is:

1. An article comprising:

a polycarbonate polymer; and a first compound of Formula (I): incorporated in the polycarbonate polymer

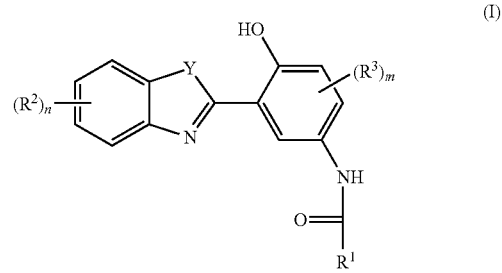

(I)

wherein $R^1$ is selected from the group consisting of an aliphatic functionality having 1 to 12 carbons, an aromatic functionality having 3 to 20 carbons, and a cycloaliphatic functionality having 3 to 20 carbons; $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3.

2. The article of claim 1, wherein the article comprises from about $1 \times 10^{-7}$ percent by weight to about 10 percent by weight of the first compound of Formula (I), based on the weight of the polycarbonate polymer.

3. The article of claim 1, wherein the first compound of Formula (I) has a Stokes shift of greater than about 50 nanometers.

4. The article of claim 1, wherein the first compound of Formula (I) is a compound selected from the group consisting of Formula (II), Formula (IV), Formula (V), Formula (VI), Formula (VIII), and Formula (IX):

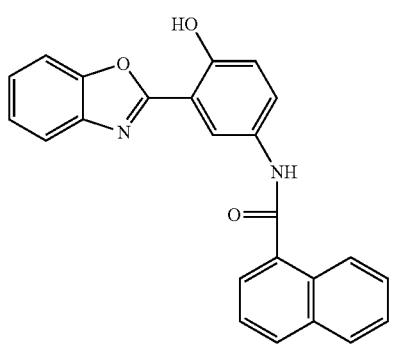
(II)

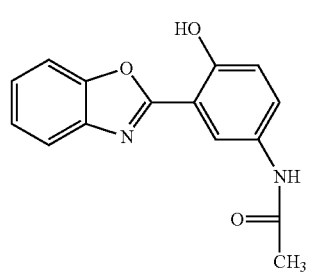
(IV)

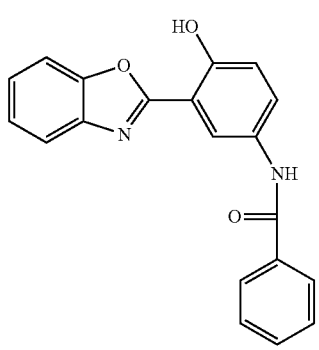
(V)

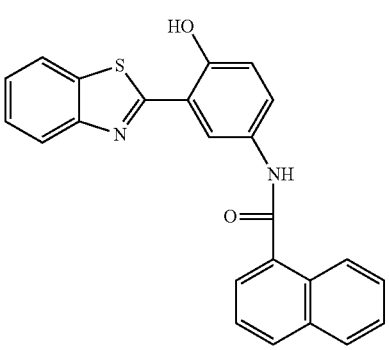
(VI)

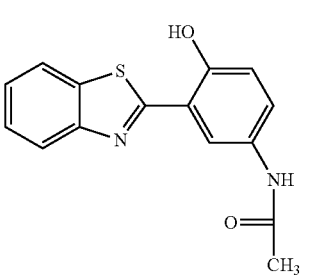
(VIII)

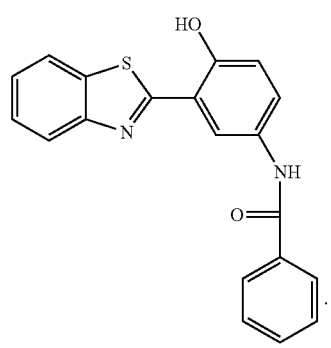
(IX)

5. The article of claim 4, wherein the first compound is of Formula (II):

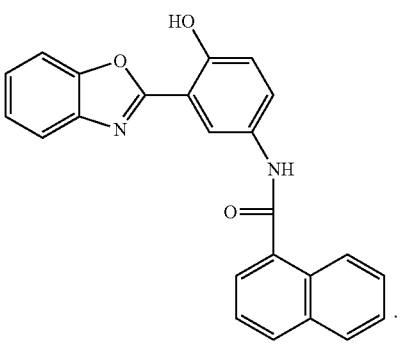
(II)

6. The article of claim 4, wherein the first compound is of Formula (VI):

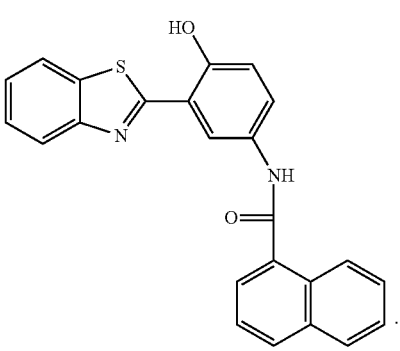
(VI)

7. The article of claim 1, wherein the article is an optical disc.

8. The article of claim 1, further comprising a second compound of Formula (I) which is different from the first compound.

9. The article of claim 1, wherein the first compound of Formula (I) has a $T_d$ of greater than 290° C.

10. The article of claim 1, wherein the first compound of Formula (I) has a $T_d$ of from 295° C. to 350° C.

11. An article made by:

incorporating an authentication compound of Formula (I) in a polycarbonate polymer to provide an authenticatable polymer;

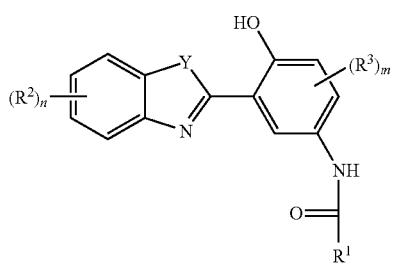
(I)

wherein $R^1$ is selected from the group consisting of an aliphatic functionality having 1 to 12 carbons, an aromatic functionality having 3 to 20 carbons, and a cycloaliphatic functionality having 3 to 20 carbons; $R^2$ and $R^3$ are independently selected from the group consisting of a hydroxyl group, a halogen atom, an aliphatic functionality having 1 to 12 carbons, an aromatic functionality having 3 to 20 carbons, and a cycloaliphatic functionality having 3 to 20 carbons; Y is either an oxygen atom or a sulfur atom; "n" has a value of 0 to 4; and "m" has a value of 0 to 3; and forming an article from the authenticatable polymer;

wherein the authentication compound of Formula (I) is present in an amount of about $1 \times 10^{-7}$ percent by weight to about 10 percent by weight based on the weight of the polycarbonate polymer.

12. The article of claim 11, wherein the article is an optical disc.

13. An article comprising:
a polycarbonate polymer; and
a compound of Formula (III), Formula (VII), or Formula (X): incorporated in the polycarbonate polymer

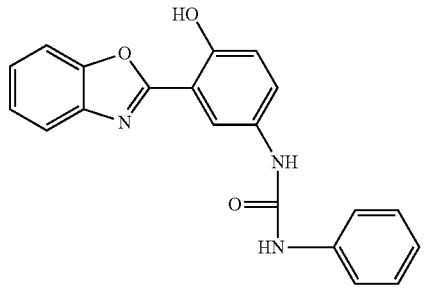
(III)

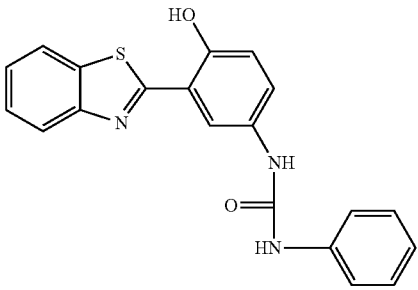
(VII)

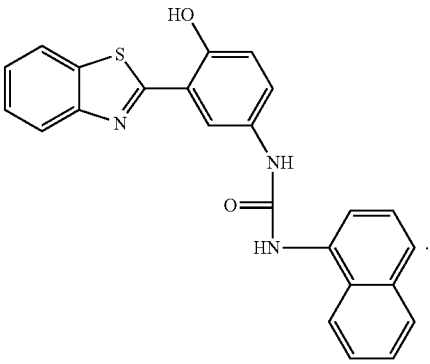
(X)

* * * * *